US007062312B2

United States Patent
Gonzales et al.

(10) Patent No.: US 7,062,312 B2
(45) Date of Patent: Jun. 13, 2006

(54) COMBINATION AND METHOD INCLUDING A VISUAL MARKER FOR DETERMINING COMPLIANCE WITH A MEDICATION REGIMEN

(75) Inventors: Gilbert R. Gonzales, New York, NY (US); Roger D. Griggs, Union, KY (US)

(73) Assignee: PediaMed Pharmaceuticals, Inc., Florence, KY (US)

( * ) Notice: Subject to any disclaimer, the term of this patent is extended or adjusted under 35 U.S.C. 154(b) by 15 days.

(21) Appl. No.: 09/765,151

(22) Filed: Jan. 17, 2001

(65) Prior Publication Data
US 2002/0095072 A1    Jul. 18, 2002

(51) Int. Cl.
  A61B 6/00   (2006.01)
  A61B 5/00   (2006.01)
  A61B 8/00   (2006.01)
  A61B 10/00  (2006.01)

(52) U.S. Cl. ......................................... 600/476; 424/9.7

(58) Field of Classification Search ................ 600/431, 600/407, 425, 476–478, 473, 160; 424/9.7, 424/10.3, 10.1, 439–442; 348/77; 514/849, 514/850, 853, 855, 900, 901, 902; 436/56, 436/169
See application file for complete search history.

(56) References Cited

U.S. PATENT DOCUMENTS

| | | | |
|---|---|---|---|
| 3,260,646 A | 7/1966 | Paulsen | |
| 3,309,274 A | 3/1967 | Brilliant | |
| 3,409,721 A * | 11/1968 | Applezweig | 514/170 |
| 3,427,377 A | 2/1969 | Bauer et al. | 424/7 |
| 3,723,613 A * | 3/1973 | Block et al. | 424/9.71 |
| 3,772,200 A | 11/1973 | Livesay | 252/301.1 R |
| 3,852,413 A * | 12/1974 | Cammarata | 424/1.69 |
| 3,928,560 A * | 12/1975 | Neely et al. | 424/52 |
| 4,152,412 A * | 5/1979 | Brewer | 424/10.3 |
| 4,390,452 A | 6/1983 | Stevens | 252/408.1 |
| 4,431,628 A * | 2/1984 | Gaffar | 424/9.71 |
| 4,568,534 A | 2/1986 | Stier et al. | 424/7.1 |
| 4,752,448 A | 6/1988 | Wells et al. | 422/56 |
| 4,875,858 A | 10/1989 | Jefferies et al. | 433/226 |
| 5,039,616 A | 8/1991 | Copelan | 436/56 |
| 5,126,145 A * | 6/1992 | Evenstad et al. | 424/465 |
| 5,179,027 A | 1/1993 | Fisher | 436/56 |
| 5,196,435 A * | 3/1993 | Clemens et al. | 514/289 |
| 5,378,634 A | 1/1995 | Sigetoh et al. | 436/91 |
| 5,458,879 A * | 10/1995 | Singh et al. | 424/400 |
| 5,547,878 A | 8/1996 | Kell | 436/111 |
| 5,652,146 A | 7/1997 | Kell | 436/111 |
| 5,776,783 A | 7/1998 | Kell | 436/111 |
| 5,882,627 A | 3/1999 | Pomerantz | 424/9.7 |
| 5,885,677 A | 3/1999 | Gosselin et al. | |
| 5,908,788 A | 6/1999 | Kell | 436/111 |
| 6,068,981 A * | 5/2000 | Rittenburg et al. | 435/7.1 |
| 6,200,604 B1 * | 3/2001 | Pather et al. | 424/466 |
| 6,303,102 B1 * | 10/2001 | Schlichte | 424/10.3 |
| 6,432,715 B1 | 8/2002 | Nelson et al. | |

FOREIGN PATENT DOCUMENTS

| | | |
|---|---|---|
| CA | 652760 | 11/1962 |
| DE | 1250969 | 8/1964 |
| GB | 1110329 | 5/1968 |
| WO | WO 9512812 | 5/1995 |
| WO | WO 9917747 | 4/1999 |
| WO | WO 0037114 | 6/2000 |
| WO | WO 02/056919 | 7/2002 |

OTHER PUBLICATIONS

Thilothammal, N. et al., *Testing Compliance of Drug Taking—A Simple Bed Side Method*, Indian Pediatrics, Mar. 1995; 32(3):295-9.
Stockert, J.C. et al., *Chromatin Fluoresence After Carmine Staining*, Stain Technology, vol. 65, No. 6, p. 299.
Morgan, Jane B., *Use of Non-Absorbable Markers in Studies of Human Nutrient Absorption*, Human Nutrition: Applied Nutrition (1986) 40A, 399-411.
Cerrato et al., *Marking of Naltrexone and Placebo Capsules with Riboflavin as an Indicator of Compliance*, Farmacia Clinica, vol. 6, No. 10, 1989, pp. 758-760.
Del Boca et al., *Assessment of Medication Compliance in Alcoholics Through UV Light Detection of a Riboflavin Tracer*, Alcoholism, Clinical and Experimental Research, United States, Nov., 1996, vol. 20, No. 8, pp. 1412-1417.
International Search Report, PCT/US02/01167, May 6, 2003.
Partial European Search Report, Jul. 23, 2004.

* cited by examiner

*Primary Examiner*—Eduardo C. Robert
*Assistant Examiner*—Anuadha Ramana
(74) *Attorney, Agent, or Firm*—Wood, Herron & Evans, L.L.P.

(57) ABSTRACT

A method and combination including a visual marker for monitoring a patient to determine compliance with a medication regimen. An orally administrable medication composition is provided in combination with a visual marker. When the combination is orally ingested, the marker causes a coloration or discoloration of the oral and/or pharyngeal cavity of a subject. By visually observing the oral and/or pharyngeal cavity of the subject, one can determine whether medication has been ingested based upon the presence or absence of the coloration/discoloration.

24 Claims, No Drawings

COMBINATION AND METHOD INCLUDING A VISUAL MARKER FOR DETERMINING COMPLIANCE WITH A MEDICATION REGIMEN

FIELD OF INVENTION

The present invention relates generally to monitoring therapeutic drug ingestion, and more particularly to a method and composition used for monitoring a patient to determine compliance by the patient with a medication regimen.

BACKGROUND OF THE INVENTION

The term "compliance" in the practice of medicine, and specifically in pharmacotherapy, is defined as the "extent to which the patient's behavior coincides with the clinical prescription" (Lift, I. F. and Chuskey, W. R., *Compliance with medical regimens during adolescence*, Pediatric Clin North Am, 27:3, 1980).

When selecting a medication for a specific patient, many factors are considered, including the medication's efficacy profile, safety profile, route of administration, price, and the compliance of the patient in taking the medication. If a medication must be taken more than once a day, compliance becomes the most important factor in selecting a drug because the pharmacologic efficacy of the medication will be more adversely affected if the medication is not taken as directed. The problem of noncompliance with a prescribed regimen has become so serious that, in response to such a problem, the pharmaceutical industry has developed long-acting forms of many medications.

The problems with noncompliance are particularly pronounced among certain groups of patients. These groups include: (1) pediatric patients, particularly those in child care centers or schools where medications are to be delivered by caregivers or teachers; (2) geriatric patients, whose caregivers are present only intermittently; (3) mentally handicapped individuals, who live independently or whose caregivers are present only intermittently; and (4) disease or disorder specific groups, including patients suffering from alcohol dependence, drug dependence, seizures, certain psychiatric conditions, cardiovascular disease, hypertension, or other conditions.

Accordingly, noncompliance is a problem that is widespread in society. Research has shown that patients only ingest half of the medication that is actually prescribed by physicians (Haynes, R. B., Taylor, D. W., and Sackett, D. L., *Compliance in Health Care*, Johns Hopkins University Press, Baltimore, 1979). Other studies have shown that up to 93% of medication regimens are not followed as prescribed (Greenberg, R. N., *Overview of patient compliance with medication dosing: A literature review*, Clin Ther, 6:592–599, 1984). The proportion of those that do not ingest their prescribed medication is greatest when social and cultural barriers, such as a language difficulty, exist, or when a decline in cognitive understanding, such as memory loss, interferes with carrying out instructions. Also, compliance varies with the illness that is treated, the degree of distress associated with symptoms, the complexity of the dosing regimen, the duration of the disease, and the extent of the adverse effects (Del Boca, F. K., Kranzler, H. R., Brown, J., and Korner, P. F., *Assessment of medication compliance in alcoholics through UV light detection of a riboflavin tracer*, Alcohol Clin Exp Res, 20(8):1412–1417, 1996; Babiker, I. E., Cooke, P. R., and Gillett, M. G., *How useful is riboflavin as a tracer of medication compliance?*, J. Behav Med, 12:25–38, 1989).

Therefore, noncompliance is a major problem in medicine in general, and in several diseases in particular. As an example, schizophrenia is associated with a noncompliance rate of 11 to 50% with an average of 33% (Maarjberg, K., Aagaard, J., and Vestergard, P., *Adherence to lithium prophylaxis:* 1. Clinical predictors and patient's reasons for non adherence, Pharmacopsychiatry 21:121–125, 1988; Kane, J. M. and Borenstein, M., *Compliance in long-term treatment of schizophrenia*, Psychopharmacol Bull, 21:23–27, 1985; Van Putten, T., *Why do schizophrenic patients refuse to take their drugs?*, Arch Gen Psychiatry, 31:67–72, 1974; Babiker, I. E., *Noncompliance in schizophrenia*, Psychiat Dev, 4:329–337, 1986). As a result, multiple areas of medicine have been subject to extensive and specific methodologic testing for compliance. For example, the use of riboflavin fluorescence in the urine has been used for testing compliance for various conditions and diseases. These include schizophrenia, clinical drug trials, alcohol dependence, iron deficiency, tricylic antidepressant therapy, hypertension medication, the use of oral contraceptives in adolescents, anti-epileptic drug use, and cardiovascular diseases (Babiker, et al., *How useful is riboflavin as a tracer of medication compliance?*, J. Behav Med, 12:25–38, 1989; Anton, *New methodologies for pharmacological treatment for alcohol dependence*, Alcohol Clin Exp Res, 20(7 Suppl): 3A–9A, 1996; Cromer, et al., *Psychosocial determinants of compliance in adolescents with iron deficiency*, Am J. Dis Child, 143(1):55–58, 1989; Gilmore, et al., *A study of drug compliance, including the effect of a treatment card, in elderly patients following discharge home from hospital*, Aging (Milano), 1(2):153–158, 1989; Perel, *Compliance during tricyclic antidepressant therapy: pharmacokinetic and analytical issues*, Clin Chem, 34(5):881–887, 1988; Sullivan, et al., *Compliance among heavy alcohol users in clinical drug trials*, J. Subst Abuse, 1(2):183–194, 1988–1989; Tinguely, et al., *Determination of compliance with riboflavin in an antidepressive therapy*, Arzneimittelforschung, 35(2):536–538, 1985; Durant, et al., *Influence of psychosocial factors on adolescent compliance with oral contraceptives*, J. Adolesc Health Care, 5(1):1–6, 1984; Jay, et al., *Riboflavin, self-report, serum norethindrone. Comparison of their use as indicators of adolescent compliance with oral contraceptives*, Am J. Dis Child, 138(1):70–73, 1984).

Other methods to determine medication regimen compliance include clinical observation of patients, and the analysis of their bodily excretions. One common method of monitoring patients for medication regimen compliance is clinical observation involving individual counseling and close personal supervision by physicians. For example, physicians may observe a patient for physiological signs and symptoms indicative of compliance or noncompliance. These signs and symptoms may include residual signs of illness. Alternatively, the patient may be interviewed regarding the degree of relief from the affliction. A physician might also evaluate physiological changes in the patient. Clinical observation, however, is time consuming and, therefore, expensive. Furthermore, it is dependent on the physician's subjective opinion, and therefore is subject to potential errors.

Still other methods of obtaining compliance information include qualitative urine monitoring methods. One example is the standard laboratory procedure known as enzyme-multiplied immunoassay (EMIT). Utilizing an arbitrary cutoff value, these methods provide the clinician with a simple positive or negative indication of the possible presence or absence of a parent drug or its metabolites in a patient's urine. Urine monitoring methods may also be used to provide a quantitative analysis of ingestion of medication. However, whether qualitative or quantitative, several drawbacks exist in these analytical methods.

First, these analytical methods and tests are time and laborintensive, often requiring the use of complex equipment in the analysis, and thus are not particularly useful when the time period between medication dosages is short. Second, these methods generally require a trained technician to perform the analysis. Third, the analysis is often performed at a location remote to the site where the sample is obtained. Finally, the sample collection itself, for example, obtaining a urine sample, involves a heightened degree of intrusiveness for the patient. As a result, these methods are not amenable to a rapid, generally non-intrusive, on-site assessment of compliance.

In an attempt to ameliorate some of the above-discussed problems of the monitoring methods of the prior art, markers have been used to determine the presence of medication in the system of a subject. However, these methods still require that the urine or stool of a subject be examined by a trained professional to detect the presence of the marker. Thus, while reducing some of the time and complexity involved, these tests are still not useful as a "home" test, still require some heightened degree of time, labor and expense, and do nothing to reduce the intrusiveness experienced by the patient.

While providing useful information relative to patient status and treatment compliance, the clinical monitoring methods described above have distinct drawbacks which limit their usefulness in determining compliance. Thus, it would be desirable to have a monitoring method that is rapid, simple, and inexpensive. Furthermore, it would be desirable for such a test to be amenable to use in the home by laypersons. Still further, it would be desirable for such a test to be minimally intrusive to the patient.

SUMMARY OF THE INVENTION

The present invention addresses the problems and drawbacks of methods and compositions of the prior art as discussed above in the Background of the Invention section. It does so by providing an orally administrable composition in combination with at least one visual marker which is present in a form and sufficient amount to cause a coloration of at least a portion of the oral and/or pharyngeal cavity of a patient. The marker can be observed visually and is present in combination with the composition in a sufficient amount and in a distinct form to cause the coloration following ingestion of the composition and the marker by the patient. For example, in one embodiment, the marker may stain a portion of the buccal membrane. The marker and/or markers may be included in the combination in many forms, such as mixed in with the composition in a pill, capsule, chewable tablet or liquid. In the alternative, the composition may be formed into a pill, capsule, or tablet with the marker subsequently coated on the outside of the composition.

In use, shortly after ingestion of the inventive combination, inspection would be carried out by visually observing the oral and/or pharyngeal cavity for a coloration or discoloration that is characteristically evoked by the marker. After the passage of time following ingestion, the visually apparent coloration or discoloration could evanesce leaving no significant coloration of a portion of the oral and/or pharyngeal cavity. In that way, multiple dosages could be monitored without the coloration from a previous dose significantly interfering with the next, subsequent dose.

Various visual inspection methods might be used. For example, the coloration might be detected under natural light with the naked eye. Alternatively, fluorescence of the oral and/or pharyngeal cavity or portion thereof could be detected using a fluorescent light. The light, which would be selected for its optimal wavelength, would evoke a visually apparent emission of fluorescence of a characteristic color for the particular marker used. The fluorescence might remain detectable for a period longer than the marker's natural coloration, such that inspection may be made after the marker coloration is no longer significantly visible to the naked eye under natural light conditions. While the naked eye should be sufficient for detection purposes, the present invention does not preclude the use of optical instruments or other detection instrumentation.

In accordance with one aspect of the present invention, the composition utilized in the combination may be a medication composition, such as a therapeutic drug, which provides the actual medicinal effects desired for the patient. Alternatively, the composition might be a placebo composition so that compliance may be tested without adversely affecting the patient. For example, the patient subject might be tested utilizing a placebo composition to determine whether they are capable of maintaining a prescribed medication regimen before the actual medication is provided.

In accordance with another aspect of the present invention, multiple markers are utilized in the combination, and the multiple markers have different coloration qualities for providing further indication of compliance. In one embodiment of the invention, one of the multiple markers causes a coloration of a portion of the oral and/or pharyngeal cavity for a longer time than another of the markers. That is, the coloration caused by one marker has a greater duration and may be visually detected, either under natural light, or fluorescent light, longer than the coloration from another marker. In that way, the presence or absence of particular colorations may be determined in order to determine a time frame in which the combination was ingested. In another embodiment of the invention, one marker may cause a different coloration than another marker. The different color markers also have different durations, such that detecting one coloration more strongly than another may indicate the length of time since the ingestion of the last dosage of the medication composition and may help establish a time frame of the last dosage.

In still another embodiment of the invention, one of the markers may cause coloration of the cavity which is detectable with natural light, while another of the markers may cause a coloration which is detectable with a light which causes fluorescence. As discussed above, the duration of the different markers may be adjusted so that an approximate time since the last dosage may be determined. In another embodiment of the invention, the multiple markers might all cause fluorescence with different fluorescent colorations so that detecting predominantly one coloration, rather another coloration, will give further information with respect to the compliance time frame and the most recent dosage.

The use of an orally ingested and visible marker provides a qualitative determination of a patient's compliance with a medication regimen. In providing for this determination rapidly, visually, and without intrusion of the patient's privacy, the present invention reduces and eliminates various of the drawbacks of the prior art. The marker can be directly visually detected soon after oral administration of the medication and also may be detected some time later by flourescing the marker in the oral and/or pharyngeal cavity.

The marker indicates to a primary caregiver, guardian, or family member whether the medication was orally ingested during a recent period of time. The presence of coloration of the oral and/or pharyngeal cavity caused by the marker is the specific information to notify the caregiver that the medication was actually orally ingested. The physical act of checking on the compliance of the medication delivery associated with the invention will also improve medication delivery.

For example, the invention will alter noncompliant behavior by notifying the patient that compliance is being monitored. Should noncompliance persist, that information would allow a caregiver to alter the methods of medication delivery. For example, a child in school or daycare who requires daytime dosing of an antibiotic for recurrent ear infections could be given an antibiotic containing the marker. The child could then be checked for ingestion compliance immediately after scheduled ingestion, or if necessary, several hours after the scheduled ingestion. The verification could occur, for example, by visual inspection of the oral and/or pharyngeal cavity immediately after the delivery under natural light or several hours later by inspection under a light which causes fluorescence.

By virtue of the foregoing, there is thus provided a method and combination composition for monitoring the compliance of a patient in following a medication regimen while reducing and/or eliminating the problems associated with monitoring methods of the prior art. The present invention reduces the time, effort, complexity, cost, and intrusiveness of prior art monitoring methods. These and other objects and advantages of the present invention shall be apparent from the accompanying Detailed Description of the Invention.

DETAILED DESCRIPTION OF THE INVENTION

The present invention comprises in combination an orally administrable composition and at least one visual marker. As described in the Summary of the Invention section, the marker of the combination is visually observable, either directly with natural light, or through fluorescence, and is present in the combination in a sufficient amount and form as to cause a coloration or discoloration/staining of at least a portion of the oral and/or pharyngeal cavity of a patient following ingestion of the combination of marker and medication or placebo composition. For example, the buccal membrane may be marked and/or the gums or tongue surface may also be marked. Other surfaces in the oral and/or pharyngeal cavity might also be marked or stained.

The present invention contemplates many different embodiments of the inventive combination and methodology. In accordance with one aspect of the present invention, the combination might utilize a medication composition which has a desired medicinal or similar effect on the patient. For example, the medication composition may have desired medicinal properties for treating a disease or symptom. In accordance with another aspect of the present invention, the compliance regimen might be determined utilizing a placebo composition in the inventive combination which has little or no medicinal effect. In that way, before the patient ingests the medication, the particular regimen, and the patient's compliance with the regimen, may be determined. For example, it may not be desirable to have a patient ingest a particular medication composition unless that patient can be relied upon to follow or comply with the regimen prescribed by a physician.

In one embodiment of the invention, a single marker may be utilized, or multiple markers might be utilized in combination with the medication or placebo composition. Utilizing at least one marker, the marker might be visually detectable either under natural light, or under an optimal exciting light with the desired wavelength to create fluorescence. To that end, the marker causes a coloration or discoloration/stain of a portion of the oral and/or pharyngeal cavity. In this application, the term "coloration" will be utilized to describe the effect of the visual marker. However, it should be understood that the term "coloration" is not limiting in its definition, and will also encompass discoloration or staining of a portion of the observed cavity in addition to a coloration which may actually match, to a certain extent, the natural coloration of the oral and/or pharyngeal cavities. For example, the marker may be detectable from its fluorescence, but may not otherwise visually discolor or stain the observed cavity. In another example, a very noticeable staining may occur. As such, the term "coloration" is used broadly herein.

A marker which is both detectable using natural light and an exciting light which causes fluorescence, provides flexibility with respect to the visual observation of a caregiver and the determination of the presence or absence of coloration caused by the marker. For example, the marker may cause a coloration which is detectable shortly after ingestion of the composition, but which may require fluorescence for detection after a certain time period has elapsed.

In accordance with one aspect of the present invention, the duration of a marker and its effects should be such that its detectable presence should generally end or at least be significantly reduced before the next dosage is due, in order to indicate to a caregiver that another dose can or should be given. Otherwise, any significant presence of the marker at the effective time for the next medication dose may make it unclear to the caregiver whether the next dose should be given. For example, medication with a half-life requiring a new dosage approximately every six hours (for example, ampicillin) should have a marker or markers that are detectable at the time of ingestion and generally for some time period after ingestion, but not significantly beyond six hours. As discussed above, the marker or markers might be detectable for a certain time period under natural light, and then may require fluorescence for the remaining time of detection. Although, in general, a detectable marker should have a duration that ends around or before the time for the next medication dosage, the duration may extend beyond that dosage time, albeit with a significantly reduced detectable presence. Therefore, the present invention is not limited to markers with any specific duration, and the markers should be tailored for a certain use. For example, a caregiver trained in compliance determination may be able to determine the time for the next dosage, even though the marker is still detectable. For example, the level of detection may indicate, based upon experience, that the last dosage was given a significant time preceding such that another dosage may be given.

In accordance with one aspect of the invention, duration of the marker and its prolonged detection may be achieved through various means. For example, the marker may be in a sufficiently high concentration in the ingested composition so as to ensure the desired duration and prolonged detection. Furthermore, encouraging patients to keep the ingested composition in their mouths longer by prolonging the swallowing time, may also affect the duration of the marker and its effective detection time. For example, a medication which is tasty or sweet may encourage children, and even adults, to maintain the composition in their mouths for a longer period of time. In another aspect of the invention, as discussed below, multiple markers might be utilized wherein each marker has a different duration. In that way, visual inspection may give the caregiver an indication of the time since the last dosage based upon the particular marker which is predominantly detectable. The various features discussed above are applicable to the situation wherein a single marker is utilized and multiple markers are utilized. As discussed further hereinbelow, multiple markers may also be utilized to provide greater flexibility in detection schemes and compliance determination.

In another embodiment of the invention, multiple markers might be utilized. Each of the multiple markers might have different coloration or duration characteristics in order to provide greater flexibility in determining compliance. More specifically, for example, multiple markers may be utilized wherein one of the markers causes a coloration of a portion of the oral and/or pharyngeal cavity for a longer time than another of the markers. A caregiver could then determine the presence or absence of colorations caused by one or more of the multiple markers to determine the time frame in which the medication or placebo combination was ingested. For example, one marker may have a duration which is approximately half of the time between recommended dosages, whereas the other marker may have a duration which lasts up to or around the end of the time period between dosages. By visually observing both markers in the inspected cavity, a caregiver will know that the composition was ingested relatively recently. If only the marker with the longer duration is detected, the caregiver will know that it has been at least a certain amount of time since the composition was ingested. In that way, a particular time frame since ingestion of the composition might be ascertained. The previous example discusses the use of two markers. However, a greater number or series of markers might be utilized to determine compliance and to more accurately pinpoint the time frame since ingestion of a medication composition, and the possible time for a new dose.

In accordance with another embodiment of the invention, multiple markers might be utilized which have different coloration characteristics, and therefore cause different coloration of the portion of the oral and/or pharyngeal cavity at issue. Different colorations may also be utilized for more accurate compliance determination, and also for determining the time frame between ingestion and doses. For example, markers having different durations may also have different colorations. Therefore, visual detection of the different markers will give an indication to the caregiver of the different marker durations which are being observed. One coloration might be predominantly observed directly after ingestion and another coloration may be predominant after a period of time.

In another embodiment of the invention, one or more of the markers may cause coloration of the oral and/or pharyngeal cavity which is detectable with natural light, whereas another of the markers may cause a coloration which is detectable only with a light that causes fluorescence. Again, the different qualities of the marker may provide for greater flexibility in determining compliance and dosing time frames. For example, the marker causing a coloration which is detectable with natural light may have a far shorter duration, whereas a marker which is detectable through fluorescence may have a longer duration. In that way, a time frame might be determined in which the composition was ingested and when the next dose might be required based upon the way the marker is detected.

In still another embodiment of the invention, multiple markers might all cause fluorescence, but with different fluorescent colorations. That is, the detection of the markers may require fluorescence. However, the particular color of the fluorescence which dominates may give an indication of the marker which is being predominantly detected. By varying the duration of such markers, further information may be ascertained through visual observation with respect to the time frame of ingestion of the composition and time frame for the next required dose in the compliance regimen.

Different types of available markers may be used in accordance with the aspects of the present invention. In one embodiment of the present invention, carmine red dye is used as a marker in combination with an orally administrable composition. The carmine red dye provides a stain of a portion of the oral and/or pharyngeal cavity and is thus used to determine whether the combination has been orally administered. This determination occurs by visual inspection either shortly after a scheduled ingestion or following the passage of a substantial amount of time after the scheduled ingestion. The discoloration or stain caused by the carmine red dye marker can be viewed either directly with the naked eye under natural white light or by fluorescing the residue of the carmine red dye in the observed cavity.

Carmine red dye is desirable as one type of marker because it is approved by the U.S. Food and Drug Administration as a color additive for use in human food with no restrictions, as a color additive in use in topical drugs, and in color additives for use in cosmetics. Therefore, it is one suitable marker in accordance with the present invention. Carmine red dye is a red or purplish-red pigment derived from cochineal beetle shells that are crushed. In addition to being visible under natural light, commercial carmine produces a strong reddish-orange fluorescence at an exciting light wave length of around 436 nanometers and again in the exciting light range of from about 450 through 490 nanometers.

Additionally, the inventors are not aware of any reported embryotoxic effects of carmine in animal studies (Grant, et al., *Tetratogenicity and embrotoxicity study of carmine of cochineal in the rat*, Food Chem Toxicol, 25(12):913–917, 1987). Carmine is considered one of the most inert and safest food additives known and is used in medical procedures, as noted in several publications (Miller and Anderson, *Silent regurgitation in day case gynaecological patients*, Anaesthesia, 43(4):321–323, 1988; Read, et al., *Transit of a meal through the stomach, small intestine, and colon in normal subjects and its role in the pathogenesis of diarrhea*, Gastroenterology, 79(6);1276–1282, 1980; Higgs, et al., *Assessment of simple methods of measuring intestinal transit times in children with gastroenteritis*, Gut, 16(6):458–461, 1975; Hallagan, et al., The safety and regulatory status of food, drug and cosmetics colour additives exempt from certification, Food Chem Toxicol, 33(6):515–528, 1995; Schmidt, *"Tagged" local anesthetic solution for transurethral surgery*, Urology, 34(5):305–306, 1989; Reece, et al., *Transabdominal needle embryofetoscopy: a new technique paving the way for early fetal therapy*, Obstet Gynecol, 84(4):305–306, 1994). Carmine red dosages up to 4,500 mg/day have been utilized. The present invention may not require such dosages, and levels in the range of approximately 100 mg/day or less may be sufficient in the applications of the present invention.

While carmine red dye is used as the marker in one embodiment of the invention, in alternate embodiments of the present invention, other dyes can be used as markers. Such dyes may include, without limitation, indigo carmine, methylene blue, tartrazine, laccaic acid, bet-carotene, FD&C blue 1, FD&C blue 2, FD&C green 3, FD&C red 3, FD&C red 40, FD&C yellow 6, and riboflavin. The dyes should be medically safe or approved and should provide a visually detectable coloration or discoloration of the oral and/or pharyngeal cavity, either under natural light or through fluorescence, as described above. Furthermore, the marker should be present in the combination with medication in an amount and form to cause detectable coloration or discoloration of the oral and/or pharyngeal cavity.

The combination of a medication or placebo composition and visual marker of the present invention may be formed into ingestable tablets, or pills by processes known in the art of pill manufacturing. Tablets may be formed either by direct compression of the composition and marker or by granulation of the components of the combination followed by compression. Pills may be formed by compressing powdered or granulated components of the combination into small diameter tablets. Alternatively, the combination may be provided in the form of a liquid. In this embodiment, both the composition and the marker are solubilized in a liquid medium where the marker is interspersed with the medication or placebo, it must be in such a form in the finished tablet, pill or liquid as to be exposed to the oral and/or pharyngeal cavity for causing the coloration or discoloration. For example, with a tablet or pill form, the marker may be exposed to the outer surface of the tablet or pill so that it directly contacts the tongue, buccal membrane, throat, and other areas of the oral and/or pharyngeal cavity. Alternatively, the tablet or pill may be chewable in order to expose more area of the observed cavities to the marker. Generally, exposure of the desired cavities to the marker will readily occur in the liquid form. Capsules, which include the combination inside, may generally pass through the readily visible area of a cavity before they dissolve. Therefore, in such a form, they may not be particularly desirable. However, the outer capsule may be suitable if it rapidly dissolves or releases dye in the oral and/or pharyngeal cavity.

In alternate embodiments of the present invention, the medication composition alone may first be formed into ingestable capsules, tablets, or pills by processes known in the art of pill manufacturing and an outer coating may then be applied which contains the marker. Capsules may be formed by filling capsules with the medication composition using conventional automatic filling equipment. Tablets may be formed either by direct compression of the medication composition or by granulation of the composition followed by compression. Pills may be formed by compressing the powdered or granulated medication composition into small diameter tablets, as discussed above. Following formation of the medication composition into capsules, tablets, or pills, the marker is then coated onto the exterior surface thereof so that it is exposed to the oral and/or pharyngeal cavity when ingested.

For example, in one embodiment of the present invention, the medication composition is provided in capsule form and the capsule is covered with a coating containing the marker. More specifically, the marker coating is added to the exterior surface of the capsule as a lacquer or coating by applying a plurality of coats to the surface of the capsule by any conventional technique. The marker coated on the surface of the capsule is applied in an amount sufficient to cause a coloration of the oral and/or pharyngeal cavity of a patient ingesting the capsule. The marker should be of such a form as to not wash away from the mucous membrane if the medication is taken with a liquid, such as water.

As noted above, while the coloration of the oral and/or pharyngeal cavity is necessary for determining compliance, it is important that the presence of the marker not have a duration which outlasts the period between medication doses. Otherwise, a coloration may exist when medication has not been ingested in compliance with a designated regimen. Such false positive results would adversely affect the accuracy of compliance testing. Thus, in accordance with one aspect of the present invention, in order to ensure that the marker does not remain visible for a longer period of time than the pharmacological efficacy of the medication composition, a marker may be chosen wherein the duration of the marker in the human system is in cooperation with the half-life of the medication composition in the human system. For example, the marker may have a duration generally equal to the medication half-life. Alternatively, multiple markers with various different durations may be used as well for different purposes, as discussed above.

The present invention also provides a method for monitoring the compliance of a patient in following a medication regimen. In this method, a patient is provided with a combination of an orally administrable composition and at least one marker. As described above, the marker or markers are present in the combination in an amount which is sufficient to cause a coloration of at least a portion of the oral and/or pharyngeal cavity of the patient. Following a scheduled dosage, the oral and/or pharyngeal cavity of the patient is then visually observed. The observer, such as a caregiver, then determines the presence or absence of coloration of the oral and/or pharyngeal cavity.

More specifically, in one example of the method of the present invention, the marker present in the combination is carmine red dye. Also, the specific portion of the oral and/or pharyngeal cavity being observed is the oral mucous membrane or buccal membrane. If the patient has actually ingested the combination of composition and marker in accordance with the principles of the present invention, then the mucous membrane will be stained with a color indicative of carmine red dye. By periodically observing the mucous membrane of the oral and/or pharyngeal cavity for this coloration, according to a determined regimen, one can determine whether a patient is following a medication regimen. Thus, if no coloration is apparent upon observation of the oral and/or pharyngeal cavity, a caregiver can either require that the patient take the proper dosage of medication, or, if refusal persists, the caregiver can alter the method of medication delivery.

Also, as described above, the oral and/or pharyngeal cavity may be observed either under natural light or under a light which causes fluorescence at an optimal exciting wavelength. More particularly, in the method of the present invention, inspection may be carried out immediately following the time for scheduled ingestion by visually observing the oral and/or pharyngeal cavity of the patient for a color that is characteristically invoked by the colored marker. This observation may be carried out under natural light and with the naked eye. In the embodiment of the present invention using carmine dye, for example, a reddish coloration would appear on a mucous membrane in the oral and/or pharyngeal cavity of the patient. If a time lapse occurs between the time scheduled for ingestion and the time of actual observation, the visually apparent color caused by the marker may evanesce, leaving little or no apparent coloring of the oral and/or pharyngeal cavity.

However, determination of ingestion of the medication composition and marker may still be obtained through fluorescence of the oral mucous membrane. In this embodiment of the method of the present invention, a flourescent light may be used to evoke a visually apparent emission of a color which is characteristic of the marker. Using carmine red dye, the reddish-orange residue left by carmine red dye would be observed. If no coloration is seen, fluorescence may still be observed in the event of partial dosage (i.e. ingestion of only part of the prescribed dosage) that might not be detected by using natural light. In order to observe the carmine red marker residue by fluorescence, an optimal exciting light is directed into the oral and/or pharyngeal cavity of the patient. To fluoresce the residue of carmine red dye, as in the one embodiment of the present invention, the light is either a violet-blue light having a wavelength of about 436 nanometers, or a blue light having a wavelength in a range of from about 450 nm to about 490 nm might be used. Moreover, as the marker evanesces, the light might be adjusted to a desirable wavelength for maximum detection of the coloration or discoloration. Therefore, an optimal exciting light in the violet-blue to blue range of about 430 nm to 490 nm may be used. Of course, lights of different appropriate wavelengths may also be used, depending upon the characteristics of the marker.

While the present invention has been illustrated by the description of various embodiments thereof, and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative combination and method, and illustrative examples shown and described. Accordingly, departures may be made from such details without departing from the spirit or scope of Applicant's general inventive concept.

The invention claimed is:

1. A method of monitoring the compliance of a patient in following a medication regimen, said method comprising the steps of:
   providing in combination an orally administrable composition, which is part of a medication regimen, and multiple markers present in said combination, one of said markers causing a contact coloration of at least a portion of a mucous membrane or buccal membrane of the oral and/or pharyngeal cavity of a patient following oral ingestion of said combination by said patient for a longer time than another of said markers, the half-life of at least one marker being comparable to the half-life of said composition;
   visually observing the oral and/or pharyngeal cavity of said patient;
   determining the presence or absence of said contact coloration for determining whether said patient has ingested said combination in compliance with the medication regimen; and
   determining the presence or absence of contact coloration caused by the multiple markers to determine a time frame in which the combination was ingested.

2. The method of claim 1 wherein said composition is a medication composition.

3. The method of claim 1 wherein said composition is a placebo composition.

4. The method of claim 1 wherein visually observing the oral and/or pharyngeal cavity of said patient to determine the presence or absence of contact coloration further comprises the step of directing natural light into the oral and/or pharyngeal cavity of said patient prior to observing the oral and/or pharyngeal cavity of said patient in order to directly observe said contact coloration.

5. The method of claim 1 wherein visually observing the oral and/or pharyngeal cavity of said patient to determine the presence or absence of contact coloration further comprises the step of directing an optimal exciting light into the oral and/or pharyngeal cavity of said patient prior to observing the oral and/or pharyngeal cavity of said patient in order to observe said contact coloration through fluorescence.

6. The method of claim 5 wherein said optimal exciting light is a violet-blue to blue light having a wavelength in a range of from about 430 nm to about 490 nm.

7. The method of claim 1 wherein visually observing said oral and/or pharyngeal cavity comprises visually observing a mucous membrane in said oral and/or pharyngeal cavity.

8. The method of claim 1 wherein said marker is carmine red dye.

9. The method of claim 1 wherein said marker is selected from the group consisting of indigo carmine, methylene blue, tartrazine, laccaic acid, beta-carotene, FD&C Blue No. 1, FD&C Blue No. 2, FD&C Green No. 3, FD&C Red No. 3, FD&C Red No. 40, FD&C Yellow No. 6, and riboflavin.

10. The method of claim 1 wherein one of said multiple markers causes a different contact coloration in the portion of the oral and/or pharyngeal cavity than another of said markers.

11. The method of claim 1 further comprising providing multiple markers in said combination wherein one of said multiple markers causes a different contact coloration in the portion of the oral and/or pharyngeal cavity than another of said markers.

12. The method of claim 1 further comprising providing multiple markers in said combination, one of said markers causing a contact coloration of a portion of the oral and/or pharyngeal cavity detectable with natural light and another of said markers causing contact coloration detectable with a light which causes fluorescence.

13. The method of claim 1 further comprising providing multiple markers in said combination, the markers being detectable with a light which causes fluorescence, one of said markers causing a different fluorescent contact coloration of a portion of the oral and/or pharyngeal cavity than the fluorescent contact coloration caused by the other marker.

14. The method of claim 1, wherein said combination is in a form and sufficient amount to cause a contact coloration directly on at least a portion of a mucous membrane or buccal membrane of the oral and/or pharyngeal cavity.

15. In combination:
   an orally administrable composition; and
   multiple markers, wherein one of said multiple markers causes a contact coloration of at least a portion of a mucous membrane or buccal membrane of the oral and/or pharyngeal cavity of a patient for a longer time than another of the markers following ingestion of said combination by said patient, the half-life of said marker being comparable to the half-life of said composition;
   said contact coloration of the oral and/or pharyngeal cavity being visually observable for determining whether said patient has ingested said combination in compliance with a medication regimen and for determining a time frame in which the combination was ingested.

16. The combination of claim 15 wherein said at least one marker is applied to the outer surface of said composition.

17. The combination of claim 15 wherein said at least one marker is interspersed throughout said composition.

18. The combination of claim 15 wherein the form of said composition is selected from the group consisting of a chewable tablet, a pill, a capsule, and a liquid.

19. The combination of claim 15 wherein said marker is operable to cause contact coloration of a mucous membrane of said oral and/or pharyngeal cavity.

20. The combination of claim 15 wherein said at least one marker is carmine red dye.

21. The combination of claim 15 wherein said at least one marker is selected from the group consisting of indigo carmine, methylene blue, tartrazine, laccaic acid, beta-carotene, FD&C Blue No. 1, FD&C Blue No. 2, FD&C Green No. 3, FD&C Red No. 3, FD&C Red No. 40, FD&C Yellow No. 6, and riboflavin.

22. The combination of claim 15 wherein one of said multiple markers causes a different contact coloration in the portion of the oral and/or pharyngeal cavity than another of said markers.

23. The combination of claim 15 wherein one of said multiple markers causes a contact coloration of a portion of the oral and/or pharyngeal cavity detectable with natural light and another of said markers causes contact coloration detectable with a light which causes fluorescence.

24. The combination of claim 15 wherein the multiple markers are detectable with a light which causes fluorescence, one of said markers causing a different fluorescent contact coloration of a portion of the oral and/or pharyngeal cavity than the fluorescent contact coloration caused by the other marker.

* * * * *